United States Patent [19]

Fazio

[11] 4,328,370

[45] May 4, 1982

[54] AMMONATION OF TRIALKANOLAMINES

[75] Inventor: Michael J. Fazio, Midland, Mich.

[73] Assignee: The Dow Chemical Company, Midland, Mich.

[21] Appl. No.: 20,891

[22] Filed: Mar. 15, 1979

[51] Int. Cl.³ .............................................. C07C 89/00
[52] U.S. Cl. ..................................... 564/486; 564/499
[58] Field of Search ........................ 260/584 R, 585 R; 564/486

[56] References Cited

U.S. PATENT DOCUMENTS

| | | | |
|---|---|---|---|
| 2,112,970 | 4/1938 | Millington | 260/583 R X |
| 2,192,523 | 3/1940 | Olin et al. | 260/583 R |
| 2,861,995 | 11/1958 | MacKenzie | 260/268 |
| 2,910,477 | 10/1959 | Long | 260/268 |
| 3,068,290 | 12/1962 | Lichienberger et al. | 260/585 R |
| 3,270,059 | 8/1966 | Winderl et al. | 260/583 R |
| 3,520,933 | 7/1970 | Adam et al. | 260/585 R |

Primary Examiner—John Doll

[57] ABSTRACT

Lower trialkanolamines such as triethanolamine and triisopropanolamine are converted to the corresponding mono- and dialkanolamine by reacting with ammonia at about 150° C.–275° C. under superatmospheric pressure in the presence of a hydrogenation catalyst. The process is particularly useful for the recovery of alkanolamine values from still bottoms of alkanolamine production processes.

8 Claims, No Drawings

AMMONATION OF TRIALKANOLAMINES

BACKGROUND OF THE INVENTION

This invention relates to the conversion of a tertiary amine to corresponding primary and secondary amines. More particularly, it relates to such conversion of a trialkanolamine by reaction with ammonia.

It is known that trialkylamines can be converted to the primary and secondary amines and secondary amines can be converted to primary amines by reaction with ammonia at moderately elevated temperatures, in the presence of a hydrogenation catalyst. Such processes are described by Millington, U.S. Pat. Nos. 2,112,970 and by Olin et al., 2,192,523. It is also known that amines containing hydroxyl groups such as monoalkanolamines and dialkanolamines react with ammonia under similar conditions to produce polyamino compounds or heterocyclic nitrogen compounds, for example, ethylenediamine, N-aminoethylethanolamine, piperazine, and related compounds, depending upon the starting material and the conditions of reaction. Processes of this kind are disclosed by MacKenzie, U.S. Pat. Nos. 2,861,995, Long 2,910,477, and Fowler, 2,519,560.

In the preparation of lower alkanolamines such as ethanolamine, isopropanolamine, and butanolamine by the reaction of an alkylene oxide with ammonia, substantial quantities of the corresponding secondary and tertiary amines are also produced, the proportions of these products depending upon the ratio of reactants used and other process conditions. However, product distribution cannot always be modified enough by the ratio of reactants to meet sales demands. When the reaction mixture is distilled to separate the various products, substantial quantities of the trialkanolamine product remain as still bottoms, the trialkanolamine content of these residues usually running about 80 to 90 percent. Although these still bottoms have some useful properties when used as such with little further treatment, it would be advantageous to be able to convert this material to other useful products and thus vary the product mix obtainable from an alkanolamine process. This invention provides an additional way to modify the product distribution by converting a lower trialkanolamine to the corresponding monoalkanolamine and dialkanolamine.

SUMMARY OF THE INVENTION

It has now been found that a lower trialkanolamine is converted to at least one of the corresponding monoalkanolamine and dialkanolamine when said trialkanolamine is contacted with at least about one mole equivalent of ammonia at about 150° C.-275° C. at superatmospheric pressure in the presence of a hydrogenation catalyst. Surprisingly, the reaction product of this process consists largely or entirely of the mono- and dialkanolamines, particularly the latter, rather than polyamino alkylene compounds or piperazine compounds which are the major products of known closely similar processes that use the mono- or dialkanolamine as the organic starting material. The process is particularly adapted to the use as starting material of a crude trialkanolamine such as that obtained as a still residue from a conventional alkanolamine manufacturing process.

DETAILED DESCRIPTION OF THE INVENTION

The term "lower trialkanolamine" as used herein means those compounds where the alkanol groups are of 2-4 carbon atoms, i.e., triethanolamine, triisopropanolamine, tributanolamine, and isomers thereof. Triethanolamine and triisopropanolamine are the more common members of the class.

Ammonia is preferably employed in molar excess over the trialkanolamine, for example, at least about two moles and preferably at least about three moles per mole of trialkanolamine. There is no real upper limit to the proportion of ammonia that can be used, but ammonia in molar proportions above about twenty to one of amine acts essentially as a diluent of the reaction mixture and so may be undesirable for that reason.

In the absence of a reaction solvent, the process temperature is preferably about 200° C.-250° C. Since a batch process is normally run at about the autogenous pressure of the reaction mixture, the usual pressure in such a system is about 100-250 atmospheres. A continuous process can be operated at a considerably lower pressure. For example, the process was run successfully in this fashion at 30-60 atmospheres. When an inert solvent for the trialkanolamine is present in the reaction mixture, the preferred process temperature is about 150° C.-200° C. with correspondingly lower pressure for a batch operation.

Although any metal-containing hydrogenation catalyst such as nickel, copper chromite, or platinum is effective to promote the desired reaction to some extent, best results are obtained with finely divided noble metals of Group VIII of the Periodic Table, particularly palladium, rhodium, and platinum. The quantity of catalyst used is not critical as any significant amount will show some catalytic effect. For batch reactions, about 0.1-2 percent of metal catalyst based on the weight of trialkanolamine is preferred. Either the finely divided metal itself or as supported on an inert support can be used effectively although a supported catalyst is preferred, particularly for a continuous process where the mixed reactants are passed through a porous bed of catalyst at the process temperature. Any inert support conventionally used for such catalysts is suitable. Examples include carbon, alumina, silica, barium carbonate, magnesia, and the like.

It has been found that the efficiency of the metal catalyst is maintained at a higher level when the reaction is run in the additional presence of hydrogen. The composition of the reaction product obtained does not appear to be significantly affected by the presence of hydrogen so this diluent is an unnecessary but optional additive which provides some benefit in higher conversion, particularly in a continuous process. The proportion of hydrogen used is noncritical but has practical limits. About 0.1-2 moles of hydrogen per mole of trialkanolamine is suitable.

Another optional additive to the reaction mixture which provides some benefit particularly in the yield of the desired mono- and dialkanolamine products, is an inert solvent for the trialkanolamine starting material. Suitable solvents are those which are inert to the reactants, particularly ammonia, and they include tertiary alkanols such as tert-butyl alcohol and tert-amyl alcohol and ethers, especially dialkyl ethers of glycols such as 1,2-dimethoxyethane, 1,2-dimethoxypropane, 1,2-diethoxyethane, and the like. A boiling point which will not interfere with separation of the components of the reaction mixture by fractional distillation is a factor in the choice of a solvent.

The reaction time or contact time required to produce a practical amount of amine conversion and a good yield of the desired mono- and diethanolamines varies somewhat according to the kind of process used. In a batch process, reaction times of 0.5–10 hours are appropriate, preferably about 1–4 hours. In a continuous process, contact times of about 0.2–2 hours give good results with a contact time of about 0.5–1.5 hours preferred. In each kind of process, longer reaction or contact times may increase the conversion of amine but also favor the formation of polyamino and heterocyclic by-products as well as tarry decomposition products.

EXAMPLE 1

Different substances were tested for catalytic activity in the ammonolysis reaction using a 90 ml capacity stainless steel rocker bomb. In these experiments, a charge of 30 g of triisopropanolamine, 5 g of catalytic substance, and 20 g of anhydrous ammonia was loaded into the bomb which was then rocked at 250° C. for three hours. The bomb was then cooled and vented, the contents were filtered to remove the catalytic substance, and the filtrate was analyzed. The results obtained are listed in Table 1. Yields and conversions in this and the other examples are based on the alkanolamine.

TABLE 1

| Catalyst | % Conversion[1] | % Yield[2] |
|---|---|---|
| None | 0 | 0 |
| $Fe_2O_3$ | 0 | 0 |
| $Al_2O_3$ | 0 | 0 |
| copper chromite | 2 | 56 |
| Raney Ni | 4 | 61 |
| 5% Pt on C | 2 | 97 |
| 5% Pd on $Al_2O_3$ | 37 | 69 |
| 5% Rh on C | 20 | 56 |
| 5% Ru on C | 10 | 64 |

[1] triisopropanolamine reacted
[2] total of mono- and diisopropanolamine based on converted triisopropanolamine

EXAMPLE 2

The reactor of Example 1 was charged with 30 g of triethanolamine, 10 g of anhydrous ammonia, and 10 g of supported catalyst as indicated below and rocked at 200° C. for two hours. The reactor was then cooled and the reaction mixture was analyzed as before. Conversions and yields are calculated as in Example 1 with the yield figures designating the total of monoethanolamine and diethanolamine found in the product calculated as a percentage of converted triethanolamine.

TABLE 2

| Catalyst | % Conversion | % Yield |
|---|---|---|
| 5% Pd on $BaCO_3$ | 2 | 99 |
| 5% Pd on C | 7 | 52 |
| 5% Pt on C | 4 | 89 |
| 5% Ru on C[1] | 8 | 55 |

[1] This reaction was carried out in the additional presence of 0.6 g mole of hydrogen per mole of triethanolamine.

EXAMPLE 3

Additional experiments were carried out as described in Example 2 using 5% Pd on $Al_2O_3$ as the catalyst and varying the reaction temperature, the ratio of ammonia to triethanolamine (TEA), and the amount of catalyst used. Three experiments were run in the additional presence of hydrogen as indicated. Conversions and yields were calculated as in Examples 1 and 2.

TABLE 3

| Wt. Ratio Charge/Catalyst[1] | Temp. °C. | Mole Ratio $NH_3$/TEA | $H_2$/TEA | % Conv. | % Yield |
|---|---|---|---|---|---|
| 2 | 200 | 3 | — | 26 | 52 |
| 4 | 200 | 3 | — | 17 | 56 |
| 6 | 200 | 3 | — | 14 | 55 |
| 8 | 200 | 3 | — | 7 | 98 |
| 6 | 200 | 9 | — | 8 | 67 |
| 4 | 250 | 3 | — | 67 | 34 |
| 4 | 250 | 3 | 0.6 | 83 | 32 |
| 4 | 200 | 3 | 0.6 | 24 | 61 |
| 4 | 200 | 3 | 1.2 | 11 | 73 |

[1] grams of TEA and ammonia per gram of catalyst

EXAMPLE 4

Experiments using an inert solvent, 5% Pd on $Al_2O_3$ catalyst, and a 3:1 molar ratio of ammonia to triethanolamine were carried out as otherwise described in the above examples. The charge to the reactor consisted of 10 g of triethanolamine, 9 g of ammonia, 38 g of solvent, and catalyst as noted. The presence of the solvent had little effect on the conversion but the yields of combined mono- and diethanolamine were considerably improved.

TABLE 4

| Solvent | Wt. Ratio TEA/catalyst | Temp. °C. | % Conv. | % Yield |
|---|---|---|---|---|
| glyme[1] | 1.3 | 200 | 28 | 87 |
| glyme | 1.3 | 190 | 24 | 87 |
| glyme | 4.5 | 190 | 10 | 93 |
| glyme | 18 | 190 | 8 | 94 |
| glyme | 1.3 | 150 | 6 | 90 |
| glyme | 4.5[2] | 190 | 3 | 93 |
| tert-butyl alcohol | 5 | 190 | 11 | 90 |

[1] glyme = 1,2-dimethoxyethane
[2] triisopropanolamine was used in place of triethanolamine

EXAMPLE 5

A reactor for continuous operation under pressure was constructed of a two foot length of 1.5 inch Incalloy 823 pipe containing a 300 ml bed of 1% Pd on carbon granules. The temperature was automatically controlled using a three zone electrical heater and the liquid ammonia-triethanolamine solution feed was pumped into the bottom of the upright pipe reactor at a metered rate. Pressure in the reactor was held at about 650–900 psig. There appeared to be a progressive loss in catalyst activity, particularly at first.

TABLE 5

| Mole Ratio $NH_3$TEA | Temp. °C. | Flow ml/min. | % Conv. | % Yield |
|---|---|---|---|---|
| 5 | 200 | 6 | 2 | 99 |
| 5 | 250 | 6 | 52 | 28 |
| 5 | 225 | 6 | 20 | 40 |
| 5 | 225 | 9 | 8 | 62 |
| 1 | 225 | 6 | 12 | 45 |
| 1 | 200 | 1 | 27 | 42 |
| 1 | 190 | 1 | 9 | 67 |

Results similar to those listed in Table 5 were obtained when the reactor was operated under the same conditions but as a trickle bed reactor with the feed solution pumped into the top of the reactor using a catalyst bed composed of 1% Pd on kaolin granules or of 1% Pd on Al$_2$O$_3$. A flow of hydrogen countercurrent to the flow of feed solution in the reactor in the latter experiments appeared to increase the conversion of triethanolamine slightly (from 14–19 percent to 16–23 percent at 200° C.).

Examples 6–8 were run in a one liter stirred autoclave using a charge of about 30 g of triethanolamine, 5 g of Pd on carbon, and ammonia to provide about a 20:1 mole ratio of NH$_3$ to triethanolamine. These reactions were run at autogenous pressure and at the indicated temperature for 4 hours, with or without the presence of hydrogen as noted. When used, hydrogen was pressured into the closed reactor at about ambient temperature to make a hydrogen pressure of 500 pounds gauge. The filtered reaction products were analyzed by vapor phase chromatography and the triethanolamine conversion and yield of monoethanolamine plus diethanolamine were calculated as in the foregoing examples.

EXAMPLE 6

These reactions show the effects of using no catalyst or a very low concentration of catalyst. Hydrogen was present in all reactions.

TABLE 6

| Catalyst | Temp., °C. | % Conversion | % Yield |
|---|---|---|---|
| none | 250 | no reaction | |
| 0.5% Pd on C | 225 | <5 | — |
| 5% Pd on C | 225 | 66.1 | 79.7 |

EXAMPLES 7–8

These examples illustrate the effects of reaction temperature with and without the presence of hydrogen. The reactions of Example 7 were run using no hydrogen and those of Example 8 were run in the presence of hydrogen added as described above. The catalyst was 5% Pd on carbon in each case.

TABLE 7

| Temp., °C. | Hydrogen | % Conversion | % Yield |
|---|---|---|---|
| 225 | none | 5.1 | 65 |
| 250 | none | 16.0 | >95[1] |
| 275 | none | 22.8 | 71[1] |
| 150 | present | no reaction | |
| 200 | present[2] | 7.2 | >95 |
| 225 | present | 66.1 | 80[3] |
| 250 | present | 86.1 | 53[4] |

[1]Small amounts of piperazine were also produced.
[2]The NH$_3$:TEA ratio was 42:1.
[3]The main by-product was 1-(2-aminoethyl) piperazine. Some piperazine was also found in the product.
[4]By-products were as in 3 plus some of unknown constitution.

I claim:

1. A process for converting a lower trialkanolamine to at least one of the corresponding monoalkanolamine and dialkanolamine which comprises contacting said trialkanolamine with at least about one mole equivalent of ammonia at about 150° C.–275° C. at superatmospheric pressure and in the presence of a hydrogenation catalyst.

2. The process of claim 1 wherein the hydrogenation catalyst is a finely divided noble metal of Group VIII of the Periodic Table.

3. The process of claim 2 wherein the trialkanolamine is dissolved in an inert solvent.

4. The process of claim 2 wherein the lower trialkanolamine is triethanolamine.

5. The process of claim 4 wherein the molar ratio of ammonia to triethanolamine is about 2–20:1.

6. The process of claim 5 wherein hydrogen is also present in the ammonia-triethanolamine reaction mixture.

7. The process of claim 4 wherein the catalyst is palladium.

8. The process of claim 2 wherein the lower trialkanolamine is triisopropanolamine.

* * * * *